United States Patent [19]
Barlow et al.

[11] Patent Number: 4,980,059
[45] Date of Patent: * Dec. 25, 1990

[54] LIQUID CHROMATOGRAPH

[75] Inventors: Derek Barlow, Cambridge; Andrew C. Cleland, St. Ives, both of England

[73] Assignee: U.S. Philips Corporation, New York, N.Y.

[*] Notice: The portion of the term of this patent subsequent to Jun. 21, 2005 has been disclaimed.

[21] Appl. No.: 368,990

[22] Filed: Jun. 19, 1989

Related U.S. Application Data

[63] Continuation of Ser. No. 94,576, Sep. 9, 1987, abandoned.

[30] Foreign Application Priority Data

Sep. 17, 1986 [GB] United Kingdom ............... 8622325

[51] Int. Cl.$^5$ .................................................. B01D 15/08
[52] U.S. Cl. ................................. 210/198.2; 210/101; 210/137; 417/22; 417/539
[58] Field of Search ................. 417/18, 22, 539; 210/101, 137, 198.2, 656, 659; 55/386

[56] References Cited

U.S. PATENT DOCUMENTS

| | | | |
|---|---|---|---|
| 3,816,029 | 6/1974 | Bowen | 417/539 |
| 3,847,507 | 11/1974 | Sakiyama | 417/22 |
| 3,981,620 | 9/1976 | Abrahams | 417/539 |
| 4,045,343 | 8/1977 | Achener | 210/101 |
| 4,127,360 | 11/1978 | Carpenter | 417/539 |
| 4,128,476 | 12/1978 | Rock | 210/101 |
| 4,311,586 | 1/1982 | Baldwin | 210/101 |
| 4,347,131 | 8/1982 | Brownlee | 210/101 |
| 4,352,636 | 10/1982 | Patterson | 417/22 |
| 4,359,312 | 11/1982 | Funke | 417/539 |
| 4,448,692 | 5/1984 | Nakamoto | 210/101 |
| 4,492,524 | 1/1985 | Koch | 210/101 |
| 4,566,858 | 1/1986 | Akiba | 417/22 |
| 4,595,495 | 6/1986 | Yotam | 417/18 |
| 4,715,786 | 12/1987 | Wolff | 417/22 |
| 4,752,385 | 6/1988 | Wilson | 210/101 |

FOREIGN PATENT DOCUMENTS

| | | | |
|---|---|---|---|
| 215525 | 3/1987 | European Pat. Off. | 210/198.2 |
| 2085980 | 5/1982 | United Kingdom | 210/198.2 |
| 2180467 | 4/1987 | United Kingdom | 210/198.2 |

*Primary Examiner*—Ernest G. Therkorn
*Attorney, Agent, or Firm*—Paul R. Miller

[57] ABSTRACT

A liquid chromatograph includes a multi piston reciprocating pump for delivering liquid at a desired flow rate to a separating column. The pistons in the pump have overlapping delivery strokes and when the pump is provided with two pistons their rate of advance is halved during the overlapping delivery periods. The instant when both pistons start delivery is dependent on solvent compressibility and the delivery pressure of the pump and thus will vary according to the operating conditions. The delivery pressure of the pump is monitored and if a pressure increase (or decrease) is found during one pump cycle between the start of stroke of one piston (SST1) and the end of delivery of the other piston (EOD2) the instant when the speed of advance of the pistons is halved (HS1) is advanced (or retarded) in the next pump cycle.

17 Claims, 11 Drawing Sheets

LIQUID CHROMATOGRAPH

This is a continuation of application Ser. No. 094,576 filed Sept. 9, 1987 now abandoned.

The invention relates to a liquid chromatograph comprising a multiple piston reciprocating pump for delivering a liquid at a desired flow rate to a separating column, each piston being arranged, during its delivery stroke, to deliver liquid at the same rate as the others, wherein the pistons are arranged to have overlapping delivery strokes and are driven by a motor whose speed is controlled by a control arrangement.

In liquid chromatography systems, and in particular high performance liquid chromatographs (HPLC), the pump is required to have a flow capability covering the range of, typically, 1 $\mu$l to 30 ml/min, a minimum internal volume so that a solvent change at the inlet to the pump rapidly reaches the column input, minimum pulsation in flow/pressure since the stability of most detection systems is adversely affected by such pulsations, and a capability of delivering at a sufficient pressure to enable the required flow of solvent through all columns likely to be used. The discharge pressure may, typically, range between 5 and 400 Bar and a variety of solvents with compressibilities typically between 50 and $150\times10^{-6}$/Bar may be used.

A variety of pumping systems are available for use in HPLC, each of which have their own advantages and disadvantages. This invention relates to chromatographs in which reciprocating piston pumps are used. Such pumps can be divided into single and multiple piston pumps. Single piston pumps have the advantage of mechanical simplicity but pose greater difficulty in achieving low pulsation in flow/pressure of the delivered liquid. With multi piston pumps it is possible to arrange that, in theory, one piston is always delivering and thus pulsation is reduced. However, due to the high pressures involved there is a significant compression of the liquid and compressible material in the pump and hence the instant at which any piston starts to deliver cannot be determined merely from the position of the piston as a degree of precompression, which varies with the particular solvent used and the system pressure, occurs before delivery commences and hence a drop in pressure will occur when one piston stops delivering before the other piston starts to deliver. One method of alleviating this problem is to monitor the pressure at the pump outlet and to increase the motor speed when the pressure falls thus minimising the period when no flow is produced by the pump and hence reducing the drop in pressure and the magnitude of the pulsations. However this requires a complex control system to drive the pump.

UK-A-2085980 discloses a liquid chromatograph as set forth in the opening paragraph which includes a regulating system for continuously varying the speed of the motor so that the pressure of the liquid conveyed remains at least approximately constant during each period.

UK Patent Application No. 8523014 corresponding to U.S. application Ser. No. 908,465, filed Sept. 17, 1986, now U.S. Pat. No. 4,752,385, discloses a liquid chromatograph as set forth in the opening paragraph characterised in that the control arrangement is arranged to produce a control signal having a characteristic of a first constant value during a first period when m of the pistons is/are delivering liquid to the column so that the piston(s) advance at a first constant velocity and a second constant value during a second period when (m+1) pistons are delivering liquid to the column to cause the pistons to advance at a second constant velocity, the second constant velocity being m/(m+1) times the first constant velocity, where m is an integer and (m+1) is less than or equal to the total number of pistons provided in the pump.

By arranging that the delivery strokes of the pistons overlap there is never a period when no piston is delivering; only a first period when m piston(s) is/are delivering and a second period when (m+1) pistons are delivering and by providing a constant rate of advance a relatively constant flow, and hence constant delivery pressure, can be obtained merely by dividing the rate of advance of the pistons by (m+1)/m during the second period. Thus, if the start and finish of the second period can be determined, a relatively simple control arrangement can be used to control the rate of advance of the pistons by merely requiring a division of the rate of advance at appropriate times.

This can be contrasted with the position disclosed in UK-A-2085980 where because the pistons do not advance with a constant linear velocity for a constant angular velocity of the cam it is necessary to continuously vary the cam velocity in order to obtain a constant flow rate. This causes considerable complexity in the regulating system.

In the chromatograph disclosed in UK Patent Application No. 8523014, corresponding to U.S. application Ser. No. 908,465, filed Sept. 17, 1986, now U.S. Pat. No. 4,752,385, the start of the second period is detected by monitoring the pressure of the liquid delivered by said pump, an increase in the pressure denoting the start of the second period.

This gives a precise indication of the start of the second period when (m+1) pistons are delivering and the instant of detection of increasing pressure can be used to divide the rate of advance of the pistons. It should be noted that while the instant when (m+1) pistons start to advance can also be easily detected, that instant cannot be used to control the speed of advance since at high delivery pressures significant precompression of the liquid takes place in the cylinder before delivery commences. The extent of the precompression will depend on the particular solvent being pumped, which may be continuously changing, and the pressure at which delivery takes place, which will depend on the column resistance and flow rate. Further it is not necessary to monitor the actual pressure since it is known that the flow rate will return to the desired value merely by dividing the rate of advance of the pistons by m/(m+1).

However, with certain systems the compressibility of the liquids and the compliance of the column and other parts of the liquid system causes the pressure increase to be relatively slow and thus the instant of speed change to be delayed as a certain pressure margin has to be allowed to avoid the change of speed being triggered by noise on the signal from the pressure transducer. This causes undesirable fluctuations in the flow rate of the liquid.

It is an object of the invention to enable the provision of a liquid chromatograph pump having a relatively simple control system which is capable of producing an output flow of liquid having comparatively low pressure pulsation.

The invention provides a liquid chromatograph as set forth in the opening paragraph characterised in that the control arrangement is arranged to produce a control signal which causes the piston(s) to advance at a first constant velocity throughout a first period when m of the pistons is/are delivering liquid to the column and at a second constant velocity throughout a second period when (m+1) of the pistons are delivering liquid to the column, the second constant velocity being m/(m+1) times the first constant velocity, where m is an integer and (m+1) is less than or equal to the total number of pistons provided in the pump; wherein the control arrangement comprises means for monitoring the delivery pressure of the pump in each pump cycle, and means for advancing the instant of change of velocity of the pistons in one cycle if a pressure increase is detected in the previous cycle or retarding the instant of change of velocity of the pistons in said one cycle if a pressure decrease is detected on the previous cycle.

In this specification the term advanced is used to specify that the speed change takes place earlier in the cycle and the term retarded is used to specify that the speed change takes place later in the cycle.

The end of the second period may be detected by monitoring the positions of the pistons. It is not necessary to detect pressure changes at the outlet of the pump to ascertain when one of the pistons ceases to deliver liquid since this is accurately known from the position of the piston. There is no problem with precompression of the liquid at this end of the delivery cycle although the filling of the cylinder during the withdrawal of the piston may be affected by decompression, both of the liquid remaining in the cylinder and in the seals and other deformable parts.

The control arrangement may comprise a microprocessor which is arranged to react to interrupt signals generated to coincide with given points in the pump cycle.

Thus the required calculations can be performed at times related to given points in the pump cycle when it is known that the necessary measurements have been made or the necessary actions taken.

The interrupt signals may be generated at the start of the delivery stroke of each piston, at the end of the delivery stroke of each piston, and at the instants of change of velocity of the pistons.

A shaft encoder, which may comprise a disc having a single cut-out and an optical detector, may be driven by the motor in synchronism with the pump and one interrupt derived from the shaft encoder.

This enables the synchronisation of the interrupt cycles with the actual position of the pump cycle once during each pump cycle. Otherwise the interrupts may get out of synchronism with the pump cycle due to, for example, any corruption of stepping pulses applied to a stepping motor driving the pump. It also enables a simple detection of a point in the pump cycle on switch on.

When the pump is driven by an electrical stepping motor, the control arrangement may produce stepping pulses for application to a driving circuit for driving the stepping motor, and at least some of the interrupt signals may then be generated as a result of counting the number of stepping pulses generated since the previous interrupt.

This avoids the need for all the interrupts to be generated by the shaft encoder which would lead to a more complex procedure for setting up the pump at the manufacturing stage and to a requirement for the shaft encoder to be more accurately synchronised with each part of the pump cycle.

The control arrangement may comprise a programmable counter, the microprocessor being arranged when each interrupt occurs to program the counter to produce an output causing the next interrupt signal to be generated a given number of stepping pulses later. The interrupt signal generated at the start of the delivery stroke of each piston may initiate the calculation of the instant of change of velocity after the start of the delivery stroke of the next piston.

The instant of change of velocity may be advanced or retarded by a time proportional to the magnitude of the pressure increase or decrease and when a stepping motor is used to drive the pump, the instant of change of velocity may be advanced or retarded by kMp steps of the stepping motor, where k is a constant and Mp is the magnitude of the pressure increase or decrease at the outlet of the pump.

This enables a quicker convergence to the correct instant for changing the motor speed. The value of the constant k may be chosen to give the best compromise between speed of convergence and stability. High values give fast convergence but low stability while low values give high stability but slow convergence.

The control arrangement may operate such that if the flow rate is increased the instant of change of velocity of the pistons on the next pump cycle is retarded by a factor dependent on the change in flow rate and if the flow rate is decreased the instant of change of velocity of the pistons on the next cycle is advanced by a factor dependent on the change in flow rate.

This reduces the time taken for convergence to the correct instant for changing speed by predicting the effect of a change of flow rate.

The second period may be terminated earlier as the flow rate is increased and later as the delivery pressure is increased.

This allows compensation for the effects of inertia which are such that the time taken between a motor speed change (doubling) and the effect of that change being reflected in the pressure trace varying under different operating conditions and particularly with different flow rates and delivery pressures.

The motor may drive the pistons through a cam arrangement. The cam arrangement may comprise a separate cam for each piston, the cams being mounted on or formed integrally with a common shaft.

A separate cam for each piston allows the pistons to be arranged side by side rather than being horizontally opposed. This simplifies the mechanical arrangement of the combining means required to combine the liquid outlets of each cylinder for feeding to the column. Having more than one piston allows more flexibility in designing the fill stroke of each piston.

The cam(s) may be profiled such that a constant angular velocity of the cam(s) produces a constant linear velocity of the delivering piston(s).

This enables a simplication of the control arrangement which simply has to ensure that the motor speed remains constant at one of two values depending on how many pistons are delivering. If the cam profiles are not formed in this manner the motor speed has to be varied to compensate for the cam characteristic. This could be achieved using a programmed memory, for example a programmable read only memory (PROM) which stores a representation of the speed correction required against cam angle to enable a constant rate of piston advance to be achieved. This enables the control arrangement to produce a constant output signal which is corrected for the cam characteristic by the contents of the PROM thus retaining a simple control arrangement but requiring a set up procedure at the manufacturing stage or if a cam is replaced.

The end of the second period may be detected by monitoring the positions of the pistons. The position of the pistons may be monitored by means of an encoder mounted on the shaft.

This enables the instant at which each of the pistons ceases to deliver liquid to be accurately detected and enables a signal to be produced to increase the speed of the motor when the end of the period is reached.

The pump may be driven by an electrical stepping motor, the characteristic of the control signal being its frequency, and during the second period in which (m+1) pistons are delivering liquid the frequency of the pulses applied to the motor is divided by (m+1)/m.

When the pump is a dual piston pump and is driven by a stepping motor the rate of advance can be halved using a simple control circuit which involves dividing the rate of the stepping pulses by two during the second period. This separates the control function for maintaining a constant flow rate from the control function which sets the desired flow rate for a particular analysis.

BRIEF DESCRIPTION OF THE DRAWINGS

An embodiment of the invention will now be described, by way of example, with reference to the accompanying drawings, in which.

DESCRIPTION OF THE PREFERRED EMBODIMENTS

Figure 1:
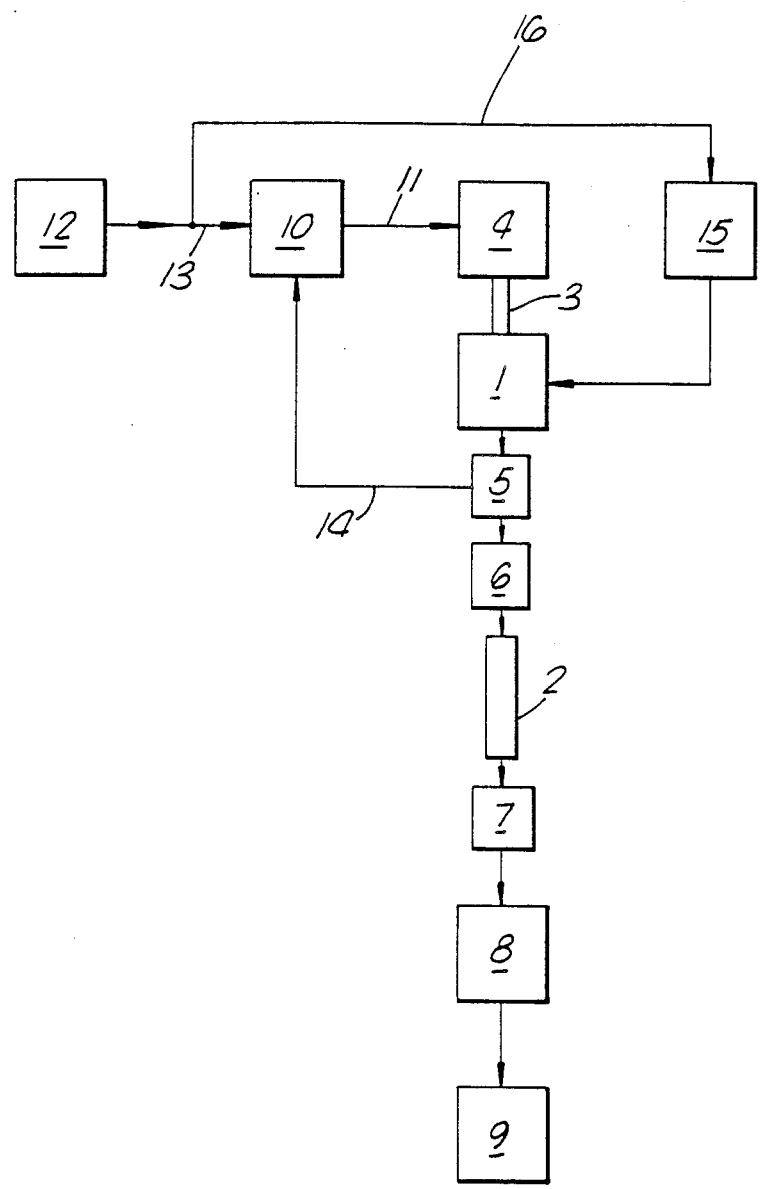
FIG. 1 shows in block schematic form a liquid chromatograph according to the invention.

FIG. 1 shows in block schematic form a liquid chromatograph which comprises a multiple piston pump 1 for pumping a liquid through a separating column 2.

The pump 1 is coupled by a shaft 3 to a stepper motor 4 which drives the pump 1. A pressure transducer 5 monitors the pressure at the outlet of the pump 1 and also connected between the outlet of the pump 1 and the inlet of the column 2 is a sample injector 6. The outlet of the column 2 is connected to a detector 7 which produces an electrical output which is fed to processing circuitry 8 which in turn drives a display device 9. The display device 9 may take any convenient form, for example a video display unit or a chart recorder. The stepper motor 4 is driven by a control circuit arrangement 10 which feeds stepping pulses at a desired rate to the stepper motor 4 over a path 11. The control circuit arrangement 10 receives a first input from an input unit 12 over a path 13. The input unit 12 may be a keyboard to allow the desired flow rate to be entered by an operator or may be any other arrangement which allows the operating parameters of the chromatograph to be set up. The control circuit arrangement 10 also receives a second input over a path 14 from the pressure transducer 5. The inlet of the pump 1 is fed from a solvent proportioning arrangement 15 which is controlled by signals from the control circuit arrangement 10 over a path 16.

In operation a desired flow rate is set up using the input unit 12 which produces signals which enable the control circuit arrangement 10 to produce stepping pulses to drive the stepper motor 4 at the appropriate speed to produce the desired flow rate when m pistons are delivering the liquid where (m+1) is less than or equal to the total number of pump pistons. The pump is arranged so that the delivery strokes of the pistons overlap to such an extent that periods of non-delivery are eliminated under worst case conditions of flow rate, pressure and compressibility for which the system is designed. Consequently under all but the worst case conditions there will be a period in each cycle when (m+1) pistons are delivering. If no further action were taken the flow rate would increase by a factor (m+1)/m and as a result the pressure at the pump outlet would increase. The outlet pressure is monitored by the pressure transducer 5 which produces a signal which is fed to the control circuit arrangement 10 over the path 14 and this information is used by the control circuit arrangement 10 to cause the rate of the stepping pulses applied to the stepper motor 4 over the path 11 to be divided by (m+1)/m when (m+1) pistons are delivering, thus reducing the rate of advance of the pistons. At the end of the period of overlapping delivery the rate at which the stepping pulses are applied to the stepper motor 4 is restored to the original value.

There are various possible ways of detecting the end of the period of overlapping delivery, for example a pressure drop at the outlet of the pump 1 can be detected by the pressure transducer 5. However, it is currently preferred to detect when each piston reaches the end of the delivery stroke with the aid of a shaft encoder where the pistons are driven by means of cams mounted on the shaft 3 driven by the stepper motor 4.

For a dual piston pump m=1 and hence when both pistons are delivering their speed of advance is halved relative to that when only one piston is delivering. This may be easily accomplished when the pulses for the stepping motor are derived digitally, for example merely switching a divide-by-two stage in or out of circuit. Where more than two pistons are provided it may be arranged that not more than two are delivering at any one time, i.e. the situation illustrated in FIG.

4(f)–(h), and in this case the speed of advance of the pistons is again halved when two are delivering relative to that when only one is delivering. The advantage of providing more than two pistons is that the return stroke of each piston can be extended allowing a longer period to fill the cylinder. This can be of particular advantage when a wide range of flow rates may be required and where a more accurate proportioning of several solvents into the cylinder is desired on each stroke. The disadvantage is, of course, greater mechanical complexity and hence cost.

An alternative arrangement when more than two pistons are provided is to arrange the pump so that more than one piston is always delivering e.g. with a four piston pump it could be arranged that at one time two pistons are delivering and that a third piston has an overlapping delivery. In this case the change of speed is one and a half times rather than twice and can thus be more quickly achieved, for a given acceleration, and consequently flow or pressure variations may be reduced.

The control circuit arrangement 10 is arranged to change the speed of the motor when (m+1) pistons start delivering by dividing its speed by the factor (m+1)/m, i.e. for a two piston pump the motor speed is divided by two. The following description assumes a two piston pump but clearly the same principles can be applied to a multi-piston pump having more than two pistons.

Figure 5:
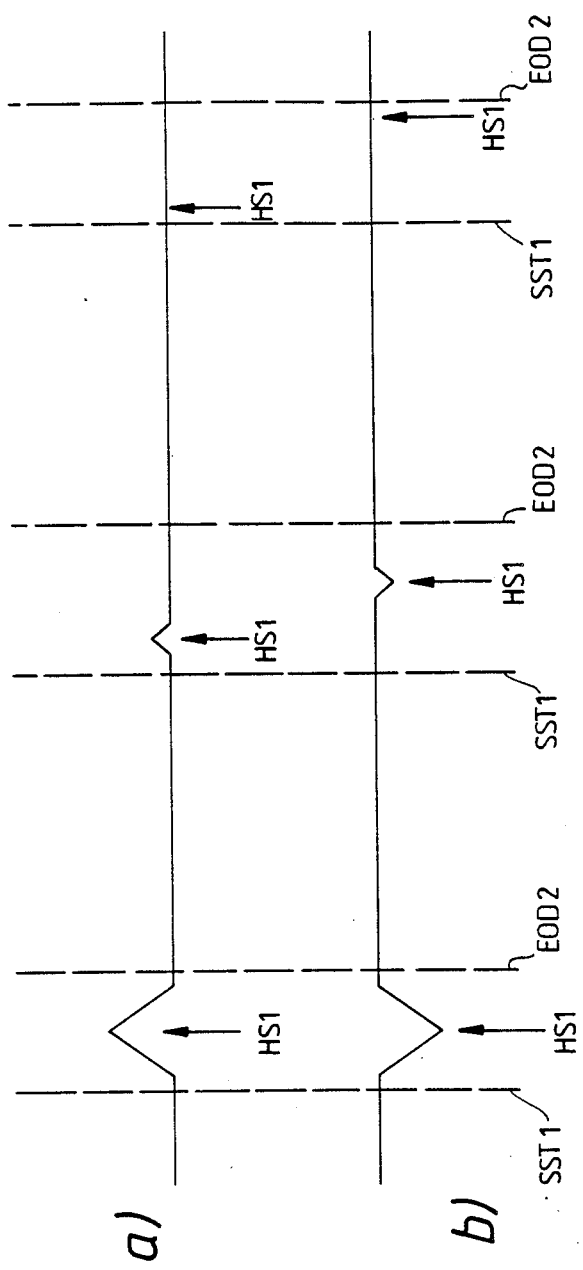
FIG. 5 shows the effect of changing the motor speed at the incorrect time and the convergence of the control circuit to the correct time.

The control circuit arrangement has an input from the pressure transducer 5 to enable the pressure to be monitored throughout the pump cycle. FIG. 5 (a) and (b) illustrate the effect of halving the motor speed too late or too early and how the correction of the instant of halving the motor speed progresses. In FIG. 5 SST1 represents the instant the first piston starts to advance, EOD2 represents the instant the second piston reaches end of delivery i.e. when it stops delivering liquid, and HS1 represents the instant at which the motor speed is halved. FIG. 5(a) illustrates the effect of halving the motor speed too late. This causes a pressure peak to be produced when both pistons are delivering. The amplitude Mp of this pressure peak is dependent on the degree of overlap of delivery of the two pistons. The control circuit arrangement 10 detects the peak and measures its amplitude and uses this information to generate an instruction to the motor to halve its speed earlier in the next pump cycle. This may be by a factor equal to kMp, where k is a constant. The value of the constant is chosen to provide the best compromise between speed of convergence and stability. A low value would produce a slow convergence which may be unacceptable when changing flow rates or solvent compositions while a high value will produce an unstable system in the presence of noise where the instant HS1 is thrown away from the desired instant by noise spikes. As can be seen from FIG. 5(a) the magnitude of the pressure peak is steadily reduced in succeeding pump cycles until it is at the level of noise on the pressure baseline signal. This is achieved by advancing the instant HS1 in response to the detection of a pressure peak on the previous pump cycle.

A similar situation occurs if the instant HS1 occurs too early except that in this case a pressure dip rather than a pressure peak is detected. The same correction procedure is followed except that the instant HS1 is retarded rather than advanced until the pressure dip is reduced to the noise level.

Clearly a similar procedure is carried out for the start of delivery of the second piston, i.e. the half speed instant HS2 between SST2 and EOD1 (the start of delivery stroke of piston two and end of delivery of piston one). If both pistons and cylinders together with the check valves are identical then the correction of the instant HS2 can be determined on the basis of the pressure increase or decrease for the delivery of the other piston. However, by making the correction dependent on the pressure during the previous cycle of the same piston the instants HS1 and HS2 for each piston can be separately adjusted to compensate for any imbalance.

As a further refinement which is particularly useful when the required flow rate is being changed and hence the outlet pressure (baseline pressure) is increasing or decreasing apart from the effect of overlapping delivery, the pressure peaks or dips and baseline pressures can be interpolated over two or more pump cycles to produce a more accurate correction. The changing baseline pressure may be caused by solvent changes or flow rate changes. Further, a predictive advance or retardation may be incorporated for compensation when the flow rate changes.

The solvent proportioning arrangement 15 receives inputs from the input unit 12 via the control circuit arrangement 10 to cause a selected solvent or mixture of solvents to be fed to the inlet of the pump. The solvent proportioning arrangement comprises a plurality of sources of solvents (for example four) which are connected via respective solenoid valves to the inlet of the pump. The solenoid valves are operated for a calculated period during the suction stroke of the pump to provide the selected solvent composition. The solenoid valves are arranged to be operated one at a time and it is ensured that no two valves are open simultaneously to prevent siphoning of different solvents through paths formed by two or more valves. An alternative possibility would be to add one way valves in each solvent inlet line to the solenoid valves.

In order to obtain the desired solvent proportions in the mixture the appropriate valves are operated in sequence for the appropriate proportion of the suction stroke of the pump. Clearly if one of the solvents is to be present in a very small proportion, for example 5 percent, then that valve will only be operated for less than 5 percent of the suction stroke. For high flow rates and small swept volume of the piston this can be difficult to achieve. As discussed in the introduction even if the valves are very quick acting the consequent fluid accelerations and decelerations may lead to out-gassing or cavitation.

The control circuit 10 and solvent proportioning arrangement 15 are constructed so that the proportioning can take place over a plurality of pump or piston cycles when the operating time of any solenoid valve is less than a given value or is likely to become less than the given value. In one arrangement this is determined by the selected flow rate produced by the pump and once a flow rate above that value is selected the solvent composition is averaged over a plurality of piston cycles. Thus if one solvent is required in a small concentration, for example 1 percent, this may be achieved by providing 5 percent of that solvent during one return stroke but only providing that solvent every fifth return stroke. An alternative method of deciding whether to average over a plurality of piston cycles is to calculate the required valve operating times to produce the required mixture in one suction stroke and to cause averaging to occur if any calculated value for a valve opening time is less than a given value.

The arrangement may also make a calculation of the actual suction volume, that is a calculation of the suction time corrected for the time taken for the unswept volume of liquid and other parts to decompress so that pressure inside the cylinder drops to atmospheric pressure. Clearly unless the solvent sources are pressurised no suction exists until the pressure in the cylinder drops to atmospheric pressure. At the delivery pressures normally involved in HPLC liquids and plastic parts are compressed by a significant amount. The decompression time is calculated from a knowledge of the precompression time on the previous delivery stroke of that piston. Once the decompression time has been calculated a precise instant for the start of suction can be determined and hence the total suction time can be accurately found. This enables a more accurate proportioning of the solvents to be achieved.

It is not essential that a multipiston pump is used as far as the invention relating to proportioning the solvents is concerned. It is equally applicable to single piston pumps and may have even more utility in such pumps since the suction time is likely to be a smaller proportion of the total pump cycle. One reason for the use of multipiston pumps is to allow a greater suction time without unacceptably increasing the flow pulsation on delivery.

Figure 2:
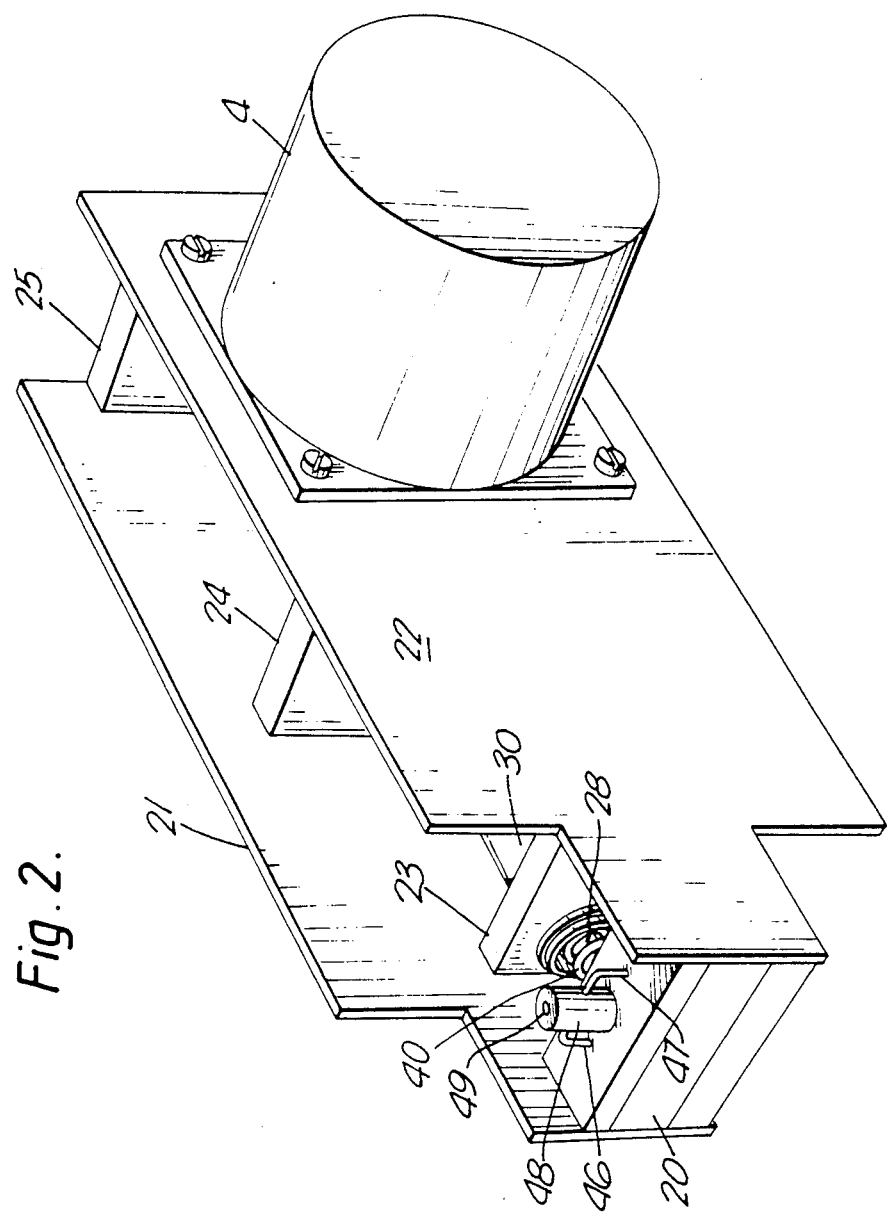
FIG. 2 is a perspective view of a pump suitable for use in the chromatograph of FIG. 1.
Figure 3:
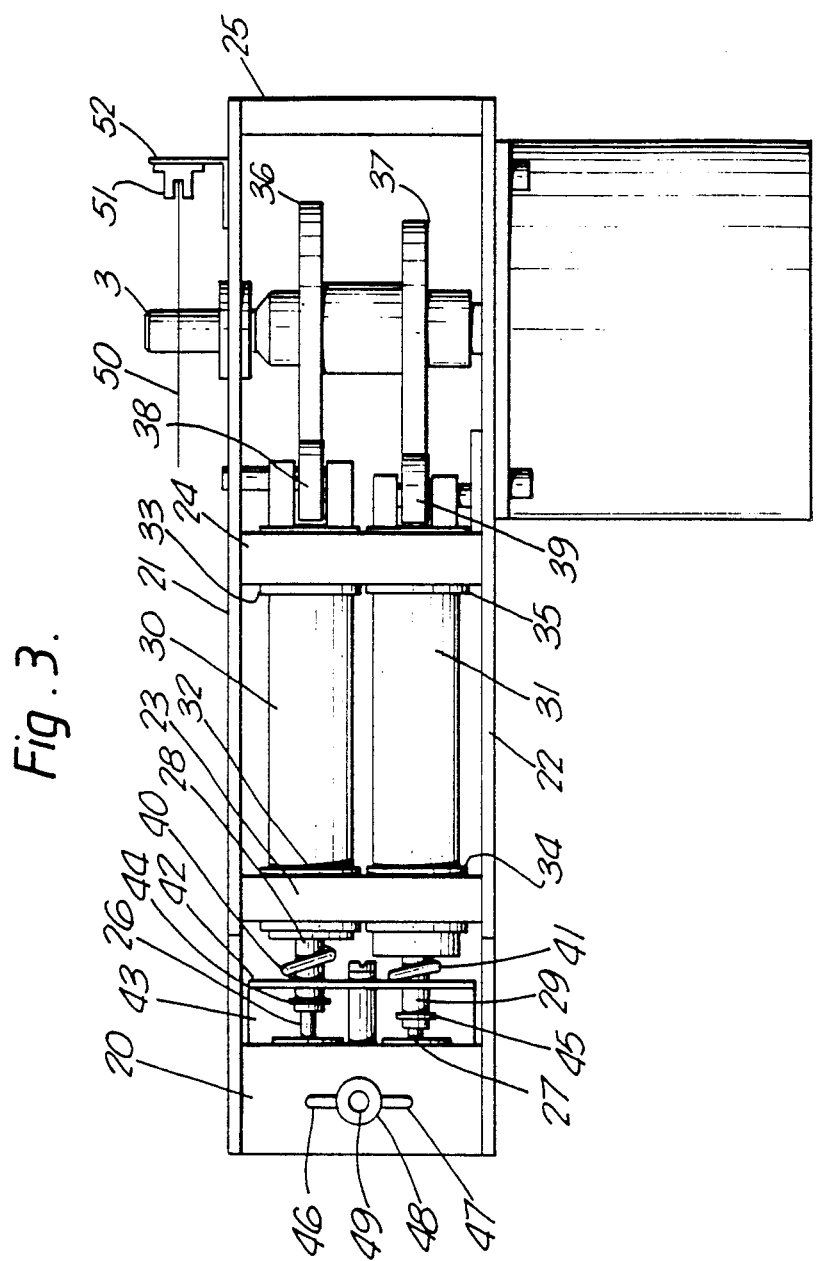
FIG. 3 is a plan view of the pump shown in FIG. 2.

FIG. 2 is a simplified perspective view of a pump 1 and motor 4 suitable for use in the chromatograph of FIG. 1 and FIG. 3 is a plan view of the pump 1 and motor 4 shown in FIG. 2.

The pump 1 comprises a pump head 20 which is clamped between two side panels 21 and 22 made from sheet metal. The pump assembly has cross pieces 24 and 25 to provide a rigid structure onto which the motor 4 and various component parts of the pump are mounted. A cross piece 23 is allowed to float between the side panels 21 and 22 so that tubes 30 and 31 which slide in bearings 32,33,34 and 35 are not constrained by any misalignment of the bearings. The pump 1 is provided with two pistons 26, 27 mounted in respective rods 28, 29 which pass into the interior of two tubes 30, 31. The tube 30 is slidably mounted in bearings 32, 33 in cross pieces 23 and 24 while the tube 31 is similarly mounted in bearings 34 and 35. Two cams 36 and 37 are mounted on the shaft 3 of the motor 4 and the tubes 30 and 31 are provided with respective cam followers 38 and 39. Coil springs 40 and 41 bias the cam followers 38 and 39 against the cams 36 and 37 by way of projections (not shown) on the rods 28 and 29, the rods 28 and 29 bearing against transverse members in the tubes 30 and 31. A transverse portion 42 of a bracket 43 provides a bearing surface for the other ends of the springs 40 and 41. Two circlips 44 and 45 are provided on the rods 28 and 29 to retain the pistons 26, 27 in the head 20 when the head is dismantled from the rest of the pump assembly. Two tubes 46, 47 take the outlets from each cylinder of the pump head 20 and combine them in a manifold 48 having an outlet 49 which forms the pump outlet. A shaft encoder 50 is attached to the shaft 3 of the motor 4 and a detector 51, which may be an opto electronic detector, is carried by a bracket 52 attached to the side panel 21 of the pump.

Figure 4:
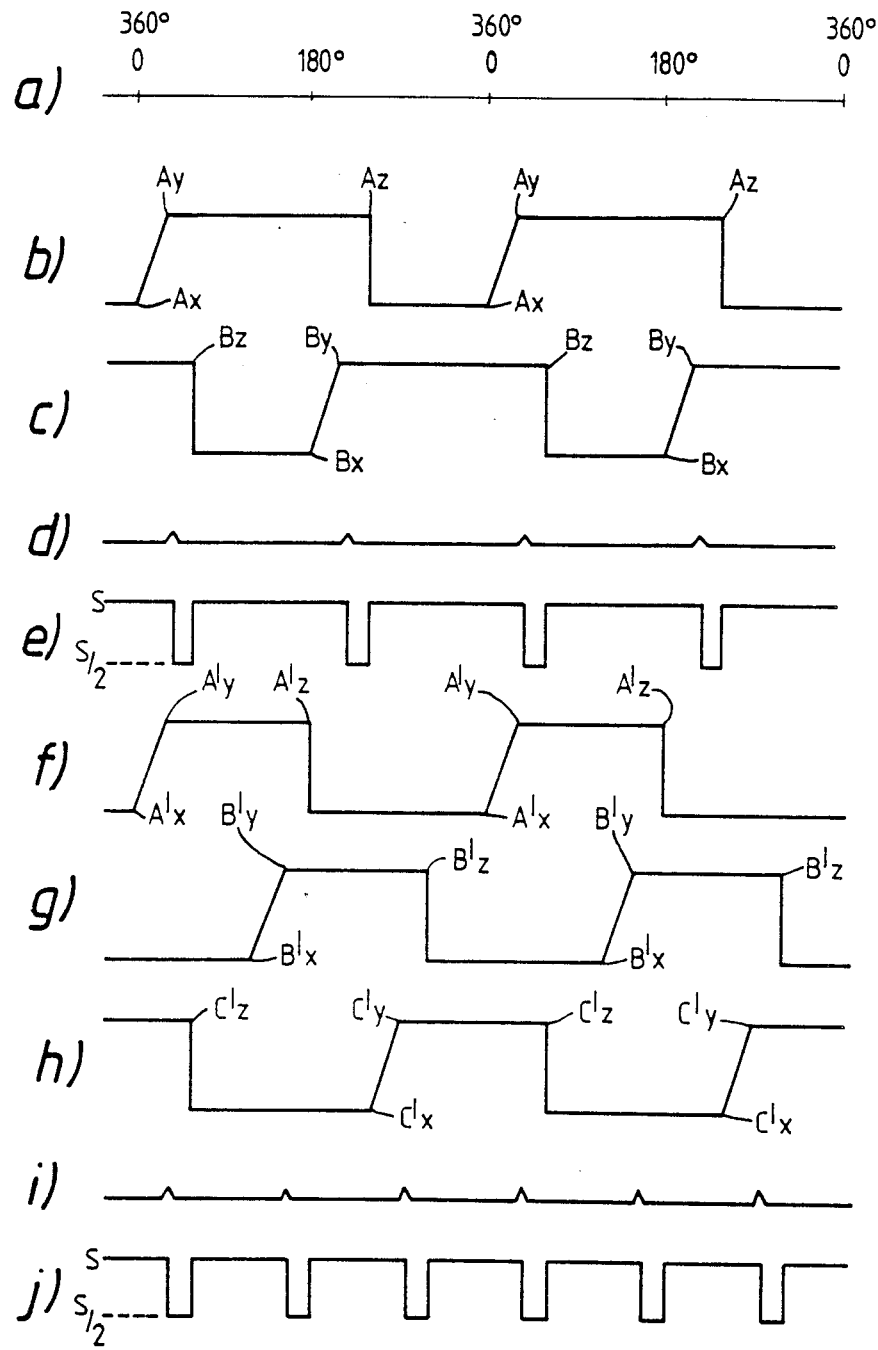
FIG. 4 illustrates the delivery of liquid by each piston of a multiple piston pump constructed for use in a liquid chromatograph.

In operation the motor 4 is supplied with stepping pulses by the control circuit arrangement 10 (FIG. 1) and causes the shaft 3 to rotate at a desired speed. As is known, by providing controlled currents to drive the stepper motor windings and ensuring the correct ratios between them the motor rotation can be incremented by several sub-steps or microsteps between each fall step. The design of a suitable stepper motor drive circuit to achieve this is well known to those skilled in that art. By utilising such a system the rotational position of the motor and its instantaneous speed can be more precisely controlled. Consequently the cams 36 and 37 cause the pistons 26 and 27 to advance and retract in accordance with the cam profiles which are designed to cause the pistons to advance on their delivery strokes at a constant linear velocity when the cams have a constant angular velocity. The design of such a cam profile is well known to those skilled in the art. As has been described with reference to FIG. 1 the pistons are arranged to have overlapping delivery strokes, i.e. there are two periods of time during each revolution of the motor when both pistons are advancing. FIG. 4 illustrates the delivery of liquid by each piston and the motor speed at various points during a pumping cycle. FIG. 4a shows the cam angles. FIG. 4b shows the pressure in the pump head due to the motion of piston 26 and shows that at point Ax the delivery stroke begins, i.e. the piston starts to advance, but that precompression of the liquid and plastic parts is occurring and no actual delivery of liquid takes place until point Ay. From point Ay until point Az delivery of liquid at a constant rate takes place since the piston is advancing at a constant linear velocity, point Az being the point at which the piston reaches the end of its delivery stroke and thus liquid can no longer be delivered. FIG. 4c shows the pressure in the pump head due to the motion of piston 27, the points Bx, By and Bz corresponding to the same points on the delivery cycle of piston 27 as points Ax, Ay and Az of piston 26. It can be seen that there is an overlap of the delivery strokes of the two pistons and that consequently unless further action is taken there will be periods during which the flow rate will be doubled. This undesirable occurrence is prevented by halving the motor speed during the overlapping delivery periods as shown in FIG. 4e which illustrates the motor speed the lower level S/2 being equivalent to half the speed of the upper level S. The instant when simultaneous delivery by the two pistons commences is predicted by monitoring the pressure at the output of the pump as is shown in FIG. 4d. When simultaneous delivery commences the pressure rises and this pressure rise is used by the control arrangement 10 to control the motor speed on the next pump cycle so that when simultaneous delivery is predicted to start on that cycle the motor speed is halved and the pressure returns to the original value since the combined delivery of the two pistons is equal to that of the original single piston delivery. The end of the period during which both pistons are delivering is detected with the aid of the shaft encoder, and at that instant the motor speed is doubled to regain its original value.

FIG. 4(f) to (j) illustrates in a similar way to FIG. 4(b) to (e) the situation where three pistons are provided in the pump and the cam profiles are such that at any one time either one or two of the pistons is/are delivering liquid. The advantage provided by the use of three pistons operating as illustrated in FIG. 4 is that a longer period is available for filling each cylinder with the solvent which is to be pumped, i.e. the period A'z to A'x is longer than the period Az to Ax. This may be of importance when several liquids are being serially fed into each cylinder to give a desired solvent mix for pumping, particularly at high flow rates when the fill time becomes shorter since the total pump cycle time becomes shorter. Thus it becomes advantageous to make the fill time as large a proportion as possible of the pump cycle time. Of course more than three pistons could be used giving even longer fill times but every added piston increases the mechanical complexity and hence cost.

Figure 6:
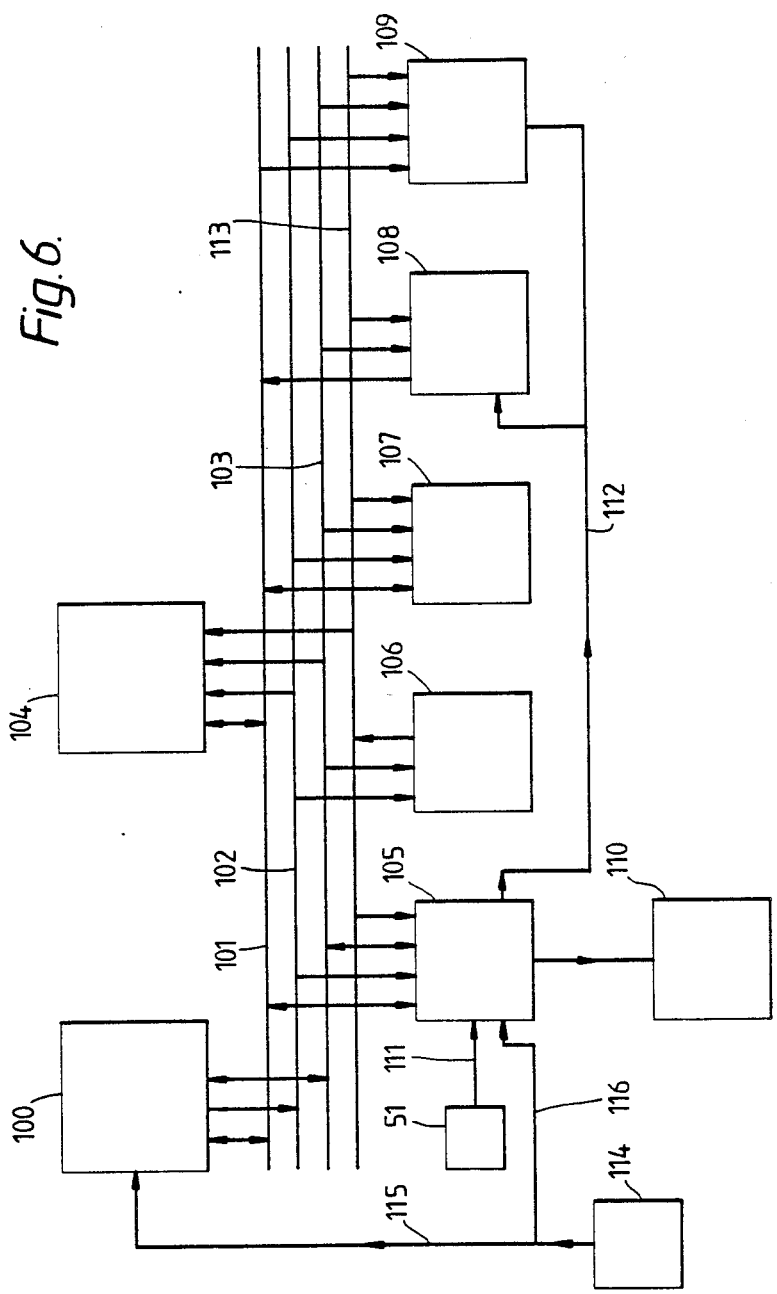
FIG. 6 shows in block schematic form one embodiment of a control circuit arrangement suitable for use in the chromatograph of FIG. 1.

The control circuit arrangement 10 shown in FIG. 6 comprises a microprocessor (CPU) 100, for example a Zilog Z80 Central Processing Unit, which is interconnected over a data bus 101, an address bus 102 and a control bus 103 with a memory 104, an interrupt generation and timing circuit (IGTC) 105, an I/O decoder (I/O DEC) 106, a keyboard and display unit (KDU) 107, a pressure monitoring unit (PMU) 108, and a solvent proportioning control unit (SMC) 109, (the unit 109 corresponds to the arrangement 15 of FIG. 1). The interrupt generation and timing circuit 105 is connected to a stepper motor drive circuit 110 which drives the motor 4 over line 11 as shown in FIG. 1. In addition the circuit 105 has an input to which the opto-detector 51 (shown in FIG. 3) is connected over a line 111, and a further output which is connected over a line 112 to the pressure monitoring unit 108 and the solvent proportioning control unit 109. The I/O decoder 106 is connected over an I/O select bus 113 to the interrupt generation and timing circuit 105, the keyboard and display unit 107, the pressure monitoring unit 108 and the solvent proportioning control unit 109. A clock generator 114 is connected over a line 115 to the microprocessor 100 and over a line 116 to the IGTC 105.

The I/O DEC 106 receives address and control signals from the microprocessor (CPU) 100 and decodes them to produce appropriate control signals for the I/O circuits which connect the blocks 105, 107, 108 and 109 to the CPU 100 and for the memory 104. The I/O DEC 106 may, for example, comprise a number of one out of eight decoder/demultiplexer chips type 74138.

Figure 7:
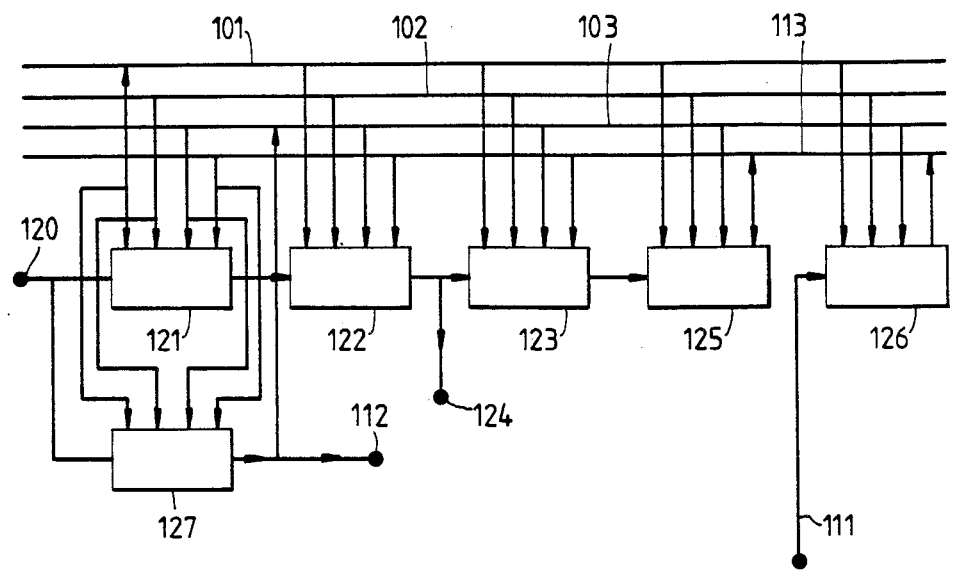
FIG. 7 shows in block schematic form an interrupt generation circuit used in the arrangement of FIG. 6.

The IGTC 105 is shown in FIG. 7 and comprises a clock input 120 which feeds a divider chain 121, 122, 123 which may be formed from a programmable interval timer (PIT) which is sold by Intel Corporation under the type reference 8254. These devices receive data from the CPU 100 over the data bus 101 under the control of the address, control and I/O select buses 102, 103 and 113. This data comprises a number to which the counters are preset so that a given division ratio is obtained. A desired flow rate for the solvent is selected by the operator by means of the KDU 107 and the CPU 100 calculates appropriate division ratios for the counters 121 and 122 so that pulses of the correct frequency to drive the stepper motor are fed to the stepper motor drive circuit 110, these pulses being derived from the output of counter 122 and being available at output 124. A divider 125 which is formed by part of a Zilog type 8430 counter timer circuit has its clock input connected to the output of counter 123 and is programmed to produce an interrupt signal on control bus 103 when the counter 123 reaches zero count. The line 111 which connects the opto-detector 51 to the IGTC 105 is connected to a divider 126 which is also formed as a Zilog Z8430 counter timer circuit and is programmed by means of signals on the address, control, data and I/O select buses to produce an interrupt signal immediately after a signal from the opto-detector is received. A further divider 127 has its clock input connected to input 120 which is fed with a clock signal from the clock generator 114 over the line 116. The divider 127 which is also formed from a Zilog type 8430 counter timer circuit is programmed to divide the clock signal so that an interrupt signal is generated every 1 msec. and is fed to the control bus 103 over line 128 and over line 112 to the pressure monitoring unit 108.

Figure 8:
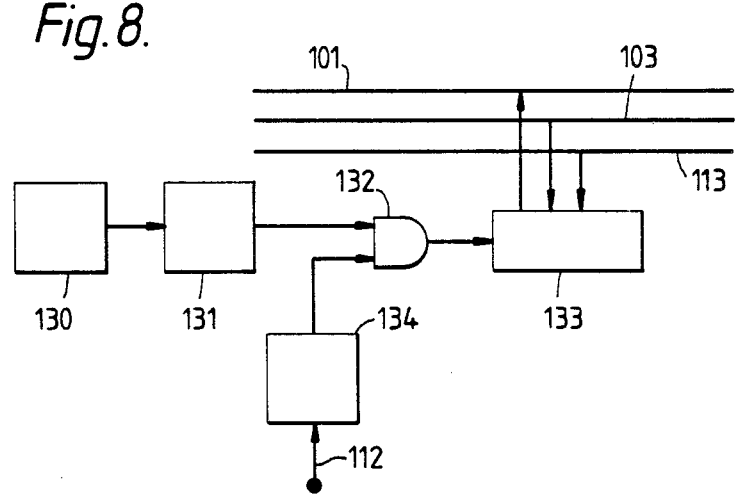
FIG. 8 shows in block schematic form a pressure monitoring arrangement used in the arrangement of FIG. 6.

The pressure monitoring unit 108 is shown in block schematic form in FIG. 8 and comprises a pressure transducer 130 which is connected to monitor the liquid pressure between the pump outlet and the column input. The pressure transducer 130 feeds a voltage to frequency (V/F) converter 131 either directly or through a current to voltage converter depending on whether the pressure transducer provides a current or voltage output. The output of the V/F converter 131 is fed to a first input of an AND gate 132 whose output is connected to the clock input of a counter 133. The counter 133 is part of an INTEL 8254 PIT and has inputs connected to the control and I/O select buses 103 and 113 and an output connected to the data bus 101. The 1 mSec pulses on line 112 are fed to a divider 134 whose output is connected to a second input of the AND-gate 132.

Figure 10:
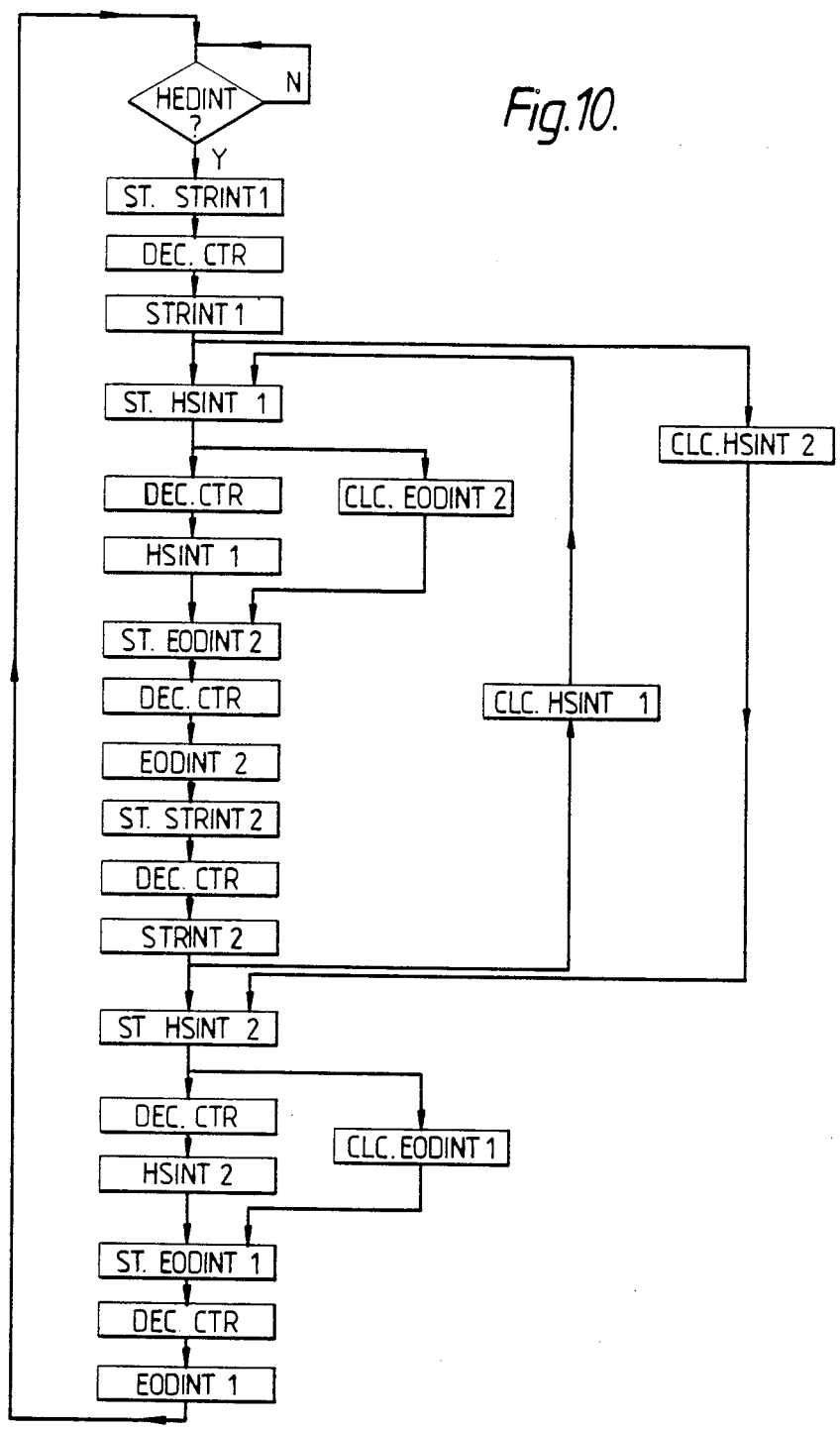
FIG. 10 shows a flow diagram illustrating the generation of interrupt signals for the microcomputer of FIG. 6.

The operation of the control circuit arrangement shown in FIGS. 6 to 8 will now be described with the aid of the flow diagram shown in FIG. 10.

The interrupt HEDINT is generated by the opto-detector and interrupt generator 126. When HEDINT occurs the microprocessor 100 sets a number into the counter 123 which corresponds to the number of microsteps of the motor 4 between the instant of HEDINT and the start of stroke of piston 26 (ST.STRINT1). This number may be generated either from a calculation based on the designed cam profile or from an initial calibration at the manufacturing stage and stored in the memory 104. The counter is clocked by the output of counter 122 (that is by the microsteps fed to the motor 4) and caused to count down to zero (DEC.CTR). The number set into the counter 123 is such that the counter 123 reaches zero when the start of stroke of piston 26 occurs. When the zero count is reached an output signal is fed to the divider 125 which generates an interrupt (STRINT1) on line 103. The interrupt STRINT1 causes two procedures to be initiated. First a number is set into the counter 123 (ST.HSINT1) which represents the number of microsteps to HSINT1 (that is the instant when the speed of the motor is to be halved) and secondly a calculation (CLC.HSINT2) is made to produce the number to be fed into the counter 123 at the corresponding point in the pump cycle for the other piston to generate HSINT2. The counter 123 is decremented (DEC.CTR) by the motor pulses generated by counter 122 and at the same time the number of motor microsteps between HSINT1 and EODINT2 is calculated, that is the number of microsteps between the instant at which the motor speed is halved and the instant at which the piston 27 ceases delivering liquid when the motor speed has to be restored to its original value. The calculation merely requires the substraction of the number of microsteps between STRINT1 and HSINT1 from the known number of microsteps between STRINT1 and EODINT2, this number being known from the cam calibration. When the counter 123 reaches zero count the interrupt HSINT1 is generated and the microprocessor 100 responds by increasing the divisor of the counter chain 121 and 122 by a factor of two to cause the rate of microstep pulses at output 124 to be divided by two and sets (ST.EODINT2) the calculated number of microsteps to EODINT2 into the counter 123. The counter 123 is decremented (DEC.CTR) by the motor pulses generated by counter 122 until the interrupt EODINT2 is generated when the counter 123 reaches its zero count. The interrupt EODINT2 causes the microprocessor 100 to restore the divisor of counters 121 and 122 to its original value since this marks the end of overlapping delivery by both pistons and to set (ST.STRINT2) the number of microsteps to the interrupt STRINT2 into the counter 123. Again this number is non-destructively accessed from the memory 104 in which it was initially entered from the known cam profile. The number corresponds to the number of microsteps of the motor between piston 27 reaching end of delivery and the start of the delivery stroke of piston 26 which is a function of the cam profile and remains constant for a given pump. The counter 123 is decremented (DEC.CTR) by the microstep pulses until the zero count is reached when the interrupt STRINT2 is generated.

The interrupt STRINT2 initiates the calculation of the half speed instant for piston 26 (CLC.HSINT1) and causes the microprocessor to set the number of microsteps to the half speed instant of piston 27 into counter 123 (ST.HSINT2). This is the value which was calculated in response to the interrupt STRINT1. The counter 123 is then decremented by the microstep pulses (DEC.CTR) and when the count reaches zero the interrupt HSINT2 is generated. In parallel with this the microprocessor calculates (CLC.EODINT1) the number of microsteps of the motor between HSINT2 and EODINT1 which corresponds to the number of steps between the half speed point and the instant at which piston 26 ceases delivering liquid.

When the interrupt HSINT2 is generated the microprocessor 100 responds by increasing the divisor of the combination of counters 121 and 122 by a factor of two to cause the motor speed to be halved and setting (ST.EODINT1) counter 123 to the calculated count (CLC.EODINT1) to the end of delivery interrupt EODINT1, that is the instant when piston 26 stops delivering liquid. The counter 123 is decremented by the microstepping pulses from counter 122 (DEC.CTR) until it reaches zero count when the interrupt EODINT1 is generated by counter 125. This interrupt causes the microprocessor 100 to set counter 125 to its maximum count. The reason for this is that the next interrupt which should be generated is HEDINT which is generated in response to the output of the opto-detector 51. Consequently by setting counter 123 to its maximum count it is ensured that this counter does not cause another interrupt signal to be generated before the next HEDINT occurs.

It would be theoretically possible to set a number into counter 123 which corresponds to the number of stepping pulses between EODINT1 and STRINT1 but using an encoder disc ensures a positive location of one instant in the pump cycle. The interrupts EODINT1 and EODINT2 which correspond to the end of delivery points of pistons 26 and 27 where the motor speed is doubled may be compensated according to the current flow rate and delivery pressure of the pump. This is necessary since the time taken between a motor speed change and the effect of that change reflected in the pressure trace varies under different operating conditions.

These compensations are carried out in the following manner:

1. Flow rate compensation.
For a maximum flow rate no adjustment is made.
For a zero flow rate a given number of microsteps are added to each EOD position.
The relationship of flow rate to compensation is assumed to be linear and to a linear interpolation between zero and the given number based on the actual flow rate is carried out.

2. Pressure compensation.
For a pressure of O Bar no adjustment is made.
For a maximum pressure a given number of microsteps are added to each EOD position.
The relationship of delivery pressure to compensation is again assumed to be linear and consequently a linear interpolation between zero and the given number based on the actual delivery pressure is carried out.

In some applications of high performance liquid chromatography (HPLC) it is necessary to change the composition of the solvent or mobile phase in a controlled manner during the analysis. For example, it may not be possible to choose a mobile phase which will enable all of the sample components to be separated and eluted in a reasonable time. This problem can be overcome by the use of a technique known as gradient elution which is analogous to temperature programming as used in gas chromatography.

Normally gradient elution involves starting the analysis with a mobile phase consisting of one particular solvent and then adding progressively increasing amounts of a second solvent during the analysis. The composition change required may involve a linear increase in the concentration of the second solvent with time or a more complex gradient may be required. However, it may also be necessary to add more than a second solvent and in some instances third and fourth solvents may be required to be mixed to produce the desired mobile phase.

It is also sometimes required to have a constant solvent mixture which may contain a small percentage of one or more particular solvents. To achieve this very short valve operating times may be required, particularly at high flow rates.

There are two main methods to obtain the desired composition of the mobile phase when using a reciprocating piston pump to produce the flow of mobile phase to the column. The first is high pressure proportioning, where the high pressure outputs of two or more pumps are combined together before being applied to the column. The individual pump flow rates are selected to give the desired composition of the solvents while the sum of their flow rates gives the desired total flow rate. The second method is to use low pressure proportioning where the solvents are proportioned by a set of solenoid valves or similar devices which are switched to give the desired mix composition. This switching or proportioning is made to happen during the suction period or periods of a single high pressure pump and the switching device is fitted in the inlet line of the pump.

Both methods have advantages and disadvantages. When low total flow rates are in use together with low percentage mixes, high pressure proportioning demands that one pump is running at a very low flow rate which is often difficult to achieve in a reproducible and reliable manner. Thus if the mix required is 99% of solvent A and 1% of solvent B then the pump supplying solvent B will be running at approximately one hundredth of the rate of the pump which is supplying solvent A.

Further, high pressure pumps are frequently controlled by means of pressure measuring devices connected at the outlet side of the pump. This can make it very difficult to connect such pumps together for high pressure mixing because of the problem of identifying which pressure measuring device is controlling which pump. Simple synchronous methods will not work if gradient elution is employed where the solvent mix composition varies as an arbitrary function of time during the chromatographic analysis.

Low pressure proportioning which is used in this embodiment has the disadvantage that the system delay volume (volume between the mixing point and the head of the chromatographic column) is larger since the whole pump volume is involved. This method is not limited at low flow rates since it becomes easier at low flow rates to proportion the solvents at the inlet to the pump. However, as flow rates increase the time allowed for proportioning the solvents into the pump is steadily decreased. Further, in order to reduce pulsations of flow at the outlet of the pump, the suction time of each piston is normally made a small proportion of the total pump cycle. Thus the time for proportioning the solvents into the inlet is correspondingly reduced. As a result the valves used to proportion the solvents to the inlet of the pump have to be very quick acting. Minimising the pump suction time increases the inlet flow rates and the consequent fluid accelerations and decelerations. This may lead to out-gassing, cavitation, or the cylinder failing to fill completely due to inertia or compressibility effects on the liquid. Any of these effects will cause errors to be produced in the solvent composition delivered at a particular flow rate.

In this embodiment the chromatograph is arranged to achieve a desired solvent composition by allowing small amounts of the different solvents into the liquid stream in succession and allowing the system volume to mix them. This is achieved by switching solenoid valves at the appropriate times to allow the required volumes of each solvent into the pump head during the return stroke.

In order to determine precisely the times at which the valves have to be switched the suction time has to be accurately determined. Theoretically, this can be accurately determined from a knowledge of the cam profile and the motor speed, i.e. the suction time will correspond to the period of the return stroke of the piston. However, in practice at the pressures used in HPLC liquids and plastics compress to a significant extent and a certain pressure differential needs to be established across the check valves before they will operate. Thus the start of the suction time does not correspond accurately with the start of the return stroke of the piston. Consequently unless a more accurate determination of the start of the suction time can be achieved a significant inaccuracy in the solvent mixture will occur, particularly at high pressures.

Figure 11:
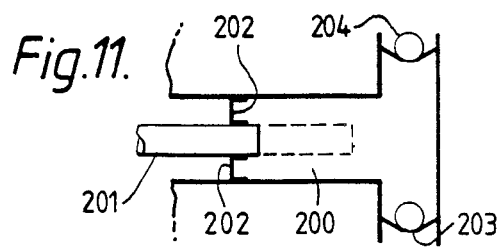
FIG. 11 is a diagrammatic cross-sectional view of one cylinder of a pump head of a typical liquid chromatograph pump.

FIG. 11 is a diagrammatic cross-sectional view of one head of a liquid chromatograph pump which comprises a cylinder 200, a piston 201, plastic seals 202 between the piston and cylinder and input and output check valves 203 and 204. As shown in FIG. 11 the piston 201 is fully retracted and the dotted rectangle shows its position when fully advanced.

At working pressures encountered in liquid chromatography (typically up to 400 bar) liquids and plastics compress to a significant extent. This causes volume loss as the rigid piston advances on its delivery since the liquid and plastic compress as the pressure in the cylinder is increased to a sufficient value to open the output check valve 204 and deliver liquid to the column at the system pressure. Similarly no suction occurs on the return stroke until the pressure within the cylinder drops to atmospheric pressure to allow the inlet check valve 203 to open.

Let it be assumed that the pump head has a stroke volume v, that is the piston swept volume denoted by the dotted rectangle, an unswept liquid volume $V_l$, and the plastic seal 202 a volume $V_p$. Further, let the liquid compressibility be $K_l$ and the plastic compressibility be $K_p$.

If we now consider precompression when the piston starts its delivery stroke we have
at zero pressure, the head volume $V(O) = V_l + v + V_p$ at pressure P, liquid volume $((V_l+v)e^{-K_lP})$ + plastic volume $(V_p e^{-K_pP}) = V(P)$ Volume loss on precompression $(PL) = V(O) - V(P)$ $PL = (V_l+v)(1-e^{-K_lP}) + V_p(1-e^{-K_pP})$ If we now consider decompression when the piston starts its return stroke we have
at pressure P, liquid volume $(V_l + V_p(1-e^{-K_pP}))$ + plastic volume $(V_p e^{-K_pP}) = V'(P)$ At zero pressure, liquid volume $((V_l + V_p(1-e^{-K_pP}))\, e^{K_lP})$ + plastic volume $(V_p) = V'(O)$ Volume loss on decompression $(DL) = V'(O) - V'(P)$ $DL = (V_l + V_p(1-e^{-K_pP}))(e^{K_lP}-1) + V_p(1-e^{-K_pP})$ The correction required is
$PL - DL = v(1-e^{-K_lP}) + V_l(2 - 2 K_lP) + V_p(e^{(K_l-K_p)P} - e^{-K_lP} - e^{-K_pP} + 1)$.
When $K_lP$ and $K_pP << 1$ Then $PL - DL \approx v\, K_l P$      1

Typically the maximum value of $K_l$ or $K_p$ is $150 \times 10^{-6}$/bar and the maximum pressure is 400 bar and therefore KP 0.06. In expression 1 the stroke volume (v) is known precisely for a given head and the system working pressure P can be measured precisely. $K_l$ is unknown for mixed solvents but typically lies between $50 \times 10^{-6}$/bar for water and $150 \times 10^{-6}$/bar for Heptane. Setting $K_l$ to be equal to $100 \times 10^{-6}$/bar gives a satisfactory result.

PL is the volume of the stroke from the start of stroke until delivery commences and can be accurately determined since, as described hereinbefore, the start of delivery can be accurately measured and is equal to the stroke between the appropriate STRINT and HSINT times multiplied by the piston area. This stroke can be determined from the cam profile and number of microsteps of the motor between STRINT and HSINT.

It should be noted that, in particular, $V_l$, $V_p$ and $K_p$ do not need to be known. Also if the plastic parts do not behave as ideal compressible solids this is compensated for. Thus, provided that the volume of stroke lost on decompression can be determined, DL can be calculated from expression 1 for any given pressure P.

Therefore, since the decompression volume can be determined the proportion of the return stroke, or suction time, taken for the unswept volume of liquid and the plastic parts to decompress can be determined since the time taken for the piston to retract a distance equivalent to the decompression volume can be determined from the known piston area, the rate of application of microstepping pulses to the motor, and the known cam profile. Thus the actual start of suction can be determined by calculating the number of microsteps from EODINT (1 or 2) which represent the decompression volume.

The decompression volume and hence the actual suction time is preferably determined separately for each piston since unless both pistons and cylinders are identical, which is difficult to achieve in practical manufacturing processes, a different precompression and decompression volume will occur in each piston/cylinder combination. This is easily achieved when the HSINT is calculated separately for each piston as has been described hereinbefore.

Figure 9:
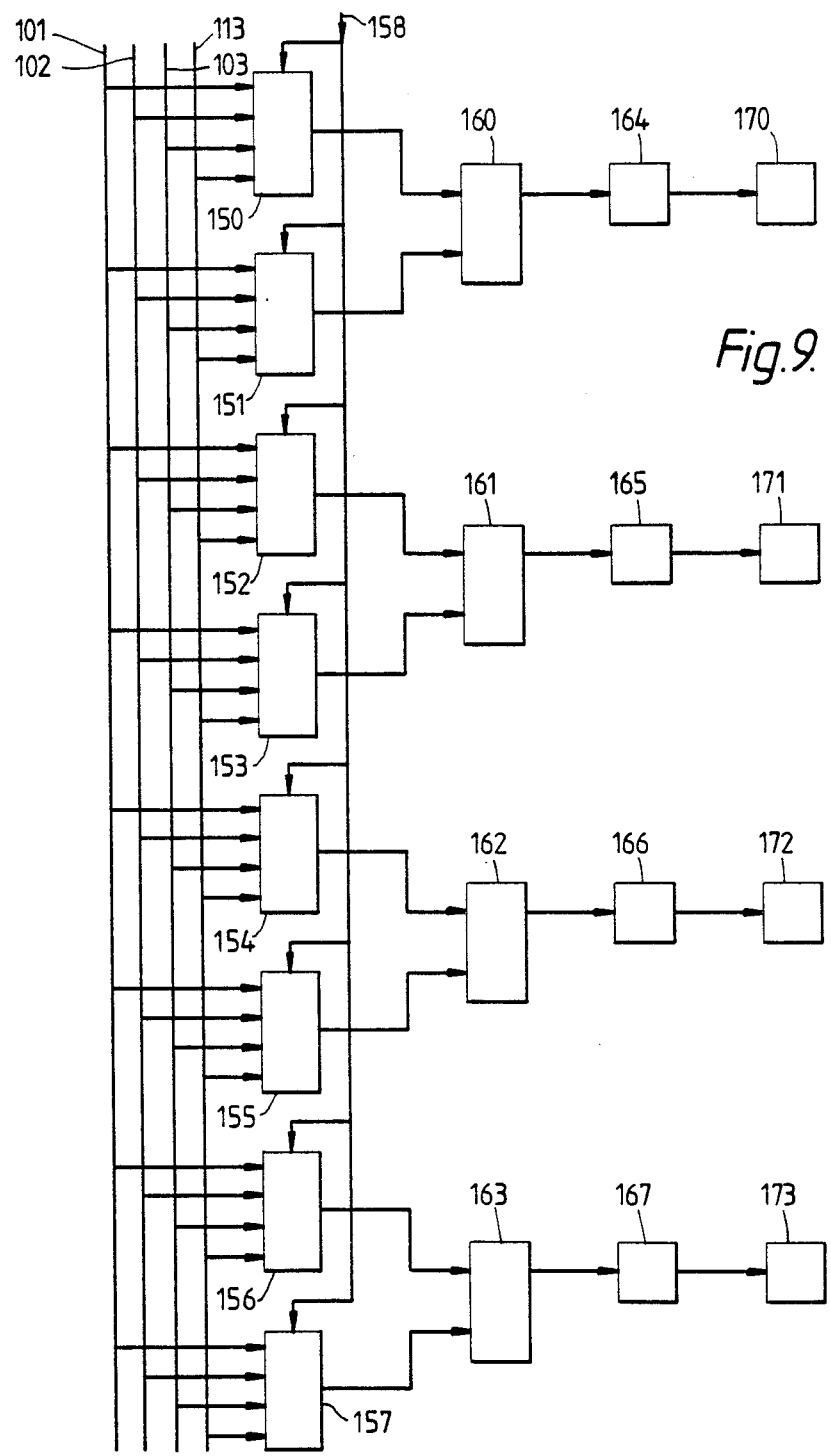
FIG. 9 shows in block schematic form a circuit for operating solvent proportioning valves used in the arrangement of FIG. 6.

FIG. 9 shows in block schematic form the solvent proportioning circuit 109 of FIG. 6. It comprises eight programmable interval timers 150 to 157 having inputs connected to the data, address, control and I/O select buses 101, 102, 103 and 113. The clock inputs of the timers 150 to 157 are fed with the microstepping pulses derived from the counter 122 in the IGTC 105 over a line 158. Four set-reset bistable circuits 160 to 163 have respective set inputs connected to the outputs of timers 150, 152, 154 and 156 and respective reset inputs connected to the outputs of timers 151, 153, 155 and 157. The outputs of the bistable circuits 160 to 163 are fed to solenoid valve driver circuits 164 to 167, respectively, while the outputs of the drive circuits are connected to respective solenoid valves 170 to 173.

In operation the microprocessor sets a count into the timers 150 to 157 and when the timers are clocked to a zero count their outputs set or reset the corresponding bistable circuits 160 to 163 and hence activate or deactivate the solenoid valves 170 to 173 at instants which depend on the initial value set into the relevant timer.

Figure 12:
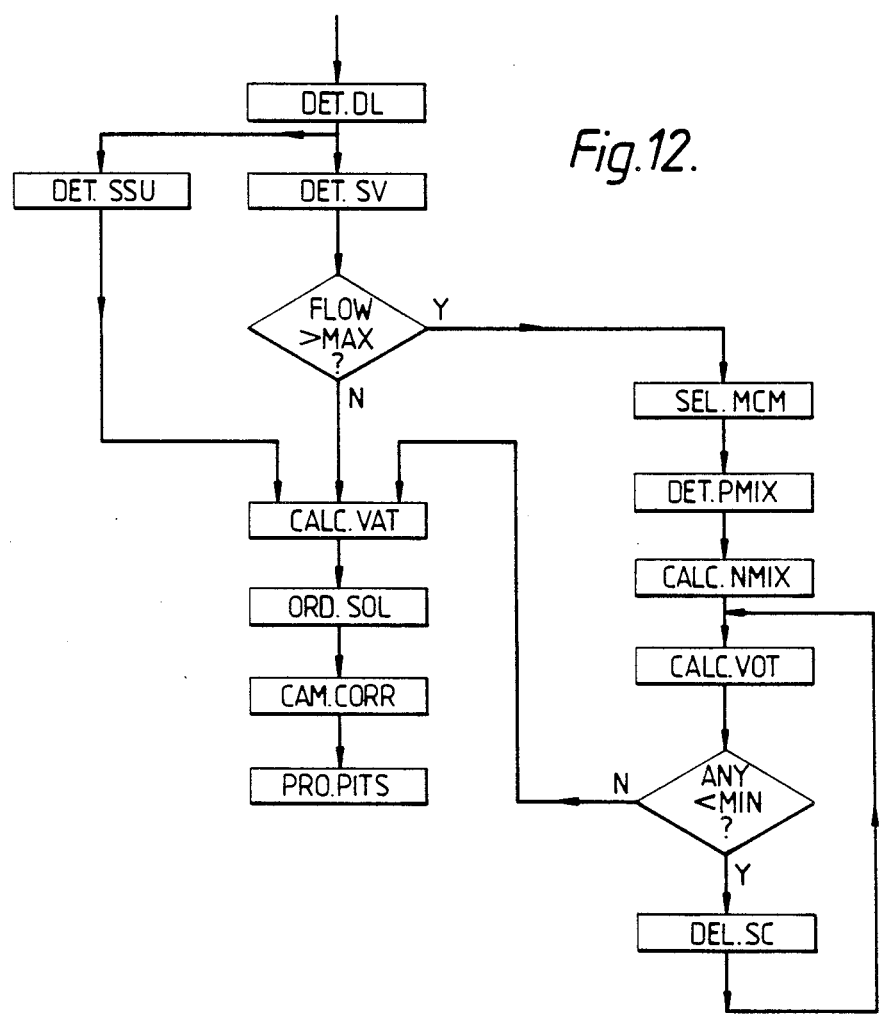
FIG. 12 shows a flow diagram illustrating the generation of control signals for the proportioning valve arrangement.

FIG. 12 shows a flow diagram illustrating the generation of the numbers to be set into the timers by the microprocessor 100. Step DET.DL comprises the calculation of the compression lost volume where the microprocessor 100 reads the numbers of microsteps from STRINT to HSINT for the delivery stroke of the piston (26 or 27) and converts this to a volume using a look-up table of cam shape stored in the memory 104. It then calculates the value vKP where v is the total piston displacement volume, K is the mean liquid compressibility (assumed to be $100 \times 10^{-6}$/bar), and P is the measured pressure. Then the volume DL=PL−vKP is calculated. Step DET SV comprises the calculation of the suction volume which is equal to the piston displacement minus the decompression volume DL.

Step DET.SSU comprises determining the instant of the actual start of the suction which is obtained from the calculated value of DL converted into microsteps which is added to EODINT.

Step CALC.VAT comprises calculating the time for which each valve must be open to produce the necessary solvent mixture. This is calculated from the suction volume, the flow rate (that is the speed of travel of the piston), the percentage of each solvent requested, and the start of suction time calculated in step DET.SSU.

Step ORD.SOL causes the order of operation of the valves to be selected so that the largest proportion solvent is split into two equal parts and the corresponding valve arranged to open at the start and the end of suction while the other solvents valves are opened in sequence between these two openings. The opening of the valve for the largest proportion solvent at the beginning of the suction stroke may take place before suction begins since the inlet check valve will be closed. Similarly the closing of that valve at the end of the suction stroke may occur after the end of the suction stroke.

Step CAM.CORR causes the valve timing, which is in terms of numbers of microsteps, to be corrected for the cam profile by means of a look-up table stored in memory 104. Step PRO.PITS comprises the setting of numbers into the programmable interval timers which correspond to the calculated valve opening and closing times for each solvent.

This procedure is satisfactory for low flow rates, that is for the decision NO to the question FLOW>MAX?, but as the flow rate is increased so the suction time decreases and if the pump displacement is small, for example 30 microliters, at flow rates of 1 ml/min and above considerably less than one second is available for proportioning the solvents. This requires extremely fast acting solenoid valves to achieve mixtures having only a small proportion (<5%) of one solvent.

A solvent proportioning system according to the invention overcomes this problem by setting a minimum value of opening time for any valve and proportioning the solvents over a plurality of piston cycles, for example sixteen piston cycles. Preferably when proportioning over a number of piston cycles a solvent mixer such as that disclosed in our co-pending U.S. application Ser. No. 94,578, filed Sept. 9, 1987, should be used to prevent unmixed slugs of one solvent of the mixture reaching the column. If the decision YES is reached to the question FLOW>MAX?, i.e. a high flow rate is requested by the operator, for example greater than 1 ml/min then the step SEL.MCM is taken. This is a procedure which causes the solvent proportioning to occur over more than one piston cycle. The procedure follows the steps DET.PMIX in which the microprocessor determines what mixture of solvents is present in the system as a result of the previous fifteen piston cycles. This is calculated from a knowledge of the valve opening times during the previous piston cycles and is calculated as a running average; CAL.NMIX in which the microprocessor calculates the proportions of each solvent which needs to be taken up during the next suction period to bring the mixture to the selected value; and CALC.VOT in which the required opening times for each of the valves is calculated to provide the proportions just calculated in CAL.NMIX. A decision is then taken ANY<MIN? to determine whether the calculated proportions require a valve opening time less than a preset minimum. If so, the smallest component is set to zero (DEL SC) and the new mixture recalculated. If not, the step CALC VAT is entered and the programmable interval timers are set as before.

Figure 13:
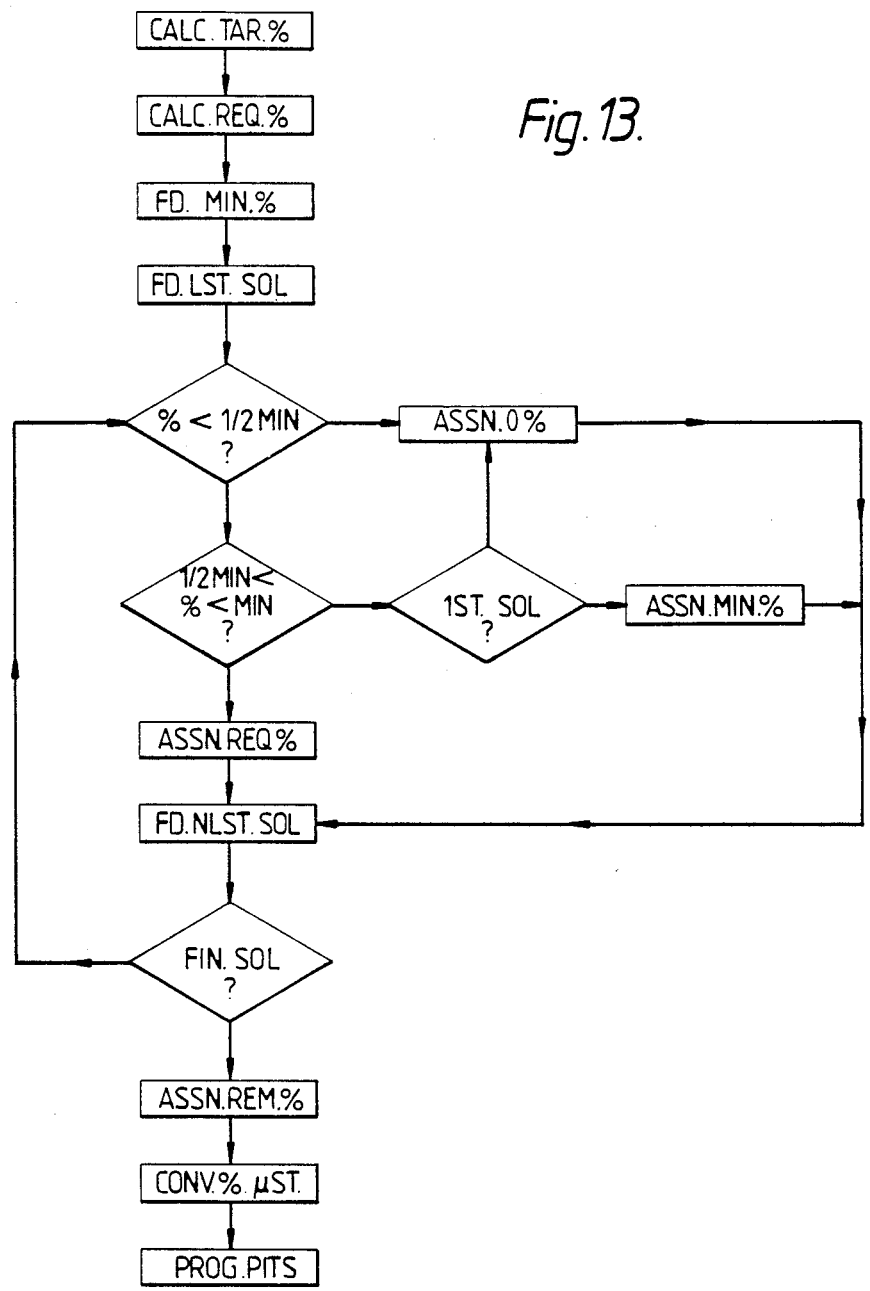
FIG. 13 shows a flow diagram of a further feature of the present invention.

FIG. 13 shows a flow diagram illustrating a second method of generating the numbers to be set into the timers by the microprocessor 100. The step CALC.-TAR% comprises the calculation of the percentage (target percentage) of each solvent which is required in the solvent mixture in accordance with the requirements set by the user. This may involve a specific constant percentage of each solvent selected by the user by means of the KDU 107 or may be calculated from a programmed gradient, i.e. a changing solvent composition with time which may be automatically calculated for each suction period by the microprocessor 100 using data entered by the user and a knowledge of the previous state of the system. The step CALC.REQ.% comprises the process of calculating the percentage of each solvent required in the next suction period to bring the current average percentage of each solvent to the value calculated in the step CALC.TAR.%. If the composition of the solvent mixture is being averaged over n piston cycles then $$\text{Required } \% = n \times \text{target } \% - (n-1) \times \text{average } \%.$$

Step FD.MIN.% comprises the calculation of the minimum percentage of any solvent which can be introduced in a suction period. This depends on the minimum valve operating time (which is set to a constant value which depends on the valves selected for the system) and the flow rate. Thus the lower the flow rate the smaller the minimum percentage can be since the suction period is correspondingly increased. The step FD.LST.SOL comprises the action of sorting the required solvent percentages into order with that requiring the lowest percentage first and in ascending order of required percentage. A decision is then made (% < ½ MIN?) as to whether the lowest percentage required of a solvent is less than half the minimum value calculated in step FD.MIN.%. If this is not the case a further decision is then taken (½ MIN < % < MIN?) as to whether the lowest percentage solvent is between the minimum value and half the minimum value. If this is not the case then the required percentage of that solvent is assigned to that solvent (ASSN.REQ.%) and stored for subsequent use in the next suction period. The step FD.NLST.SOL selects the solvent having the next lowest proportion. A decision is then taken to determine whether this is the final solvent of the mixture (FIN.SOL?) and if so the step ASSN.REM.% is taken and the remaining percentage of the suction period is assigned to the final solvent. The step CONV.%.µST comprises converting the percentage suction periods assigned to each solvent into microsteps of the motor. The actual suction period calculated as described hereinbefore can be converted into microsteps of the motor and vice versa from a knowledge of the flow rate and hence the motor speed. It is convenient to work in terms of motor microsteps since the suction period will be equivalent to a given number of microsteps dependent on the construction of the motor and pump.

The procedure just described shows the sequence of operations for solvent proportioning when the flow rate and proportions are such that each solvent can be proportioned within a single piston return stroke. However at high flow rates or with small proportions of one or more solvents this may not be. In these cases the solvent composition is achieved by averaging the individual solvent percentages over two or more piston cycles. Thus if the lowest percentage solvent requires a valve operating time of less than half the minimum valve operating time the answer YES is given to the decision % < MIN?. This causes the step ASSN.0% to be taken which step causes the valve associated with that solvent to remain closed for the next suction period. The next lowest percentage solvent is then found (FD.NLST.SOL) and unless this is the final solvent the decision % < MIN is again taken for the next lowest percentage solvent. This procedure is repeated until the answer NO is given to the decision % < MIN?

If no further solvent proportion is less than half the minimum a further decision is taken as to whether the lowest percentage proportion is between the minimum and half the minimum value. If the answer is YES then a further decision is taken as to whether this is the first solvent for which that applies (1ST.SOL?) and if the answer is YES then this solvent is assigned the minimum valve operating time (ASSN.MIN.%) for the next suction period. If the answer is NO then step ASSN.0% is taken.

Thus once any solvent percentage is required which needs a valve operating time of less than the minimum value the arrangement will cause the solvent composition to be averaged over more than one piston cycle. The number of piston cycles over which the averaging takes place will vary according to the proportions required and this will take place automatically by means of the target and required percentage calculations. The microprocessor 100 keeps a record of the assigned percentages of the solvents in each piston cycle so that the averaging can take place. The minimum number of cycles over which the averaging can take place will depend on the number of previous piston cycle assignments stored and the actual number of cycles over which the averaging takes place will depend on the actual proportions required.

It should be noted that, depending on the number of microsteps of the motor, the percentage required may not be precisely obtainable in whole numbers of microsteps. This error can also be averaged over a plurality of pump cycles to increase the precision of the solvent composition.

It may also be desirable when performing gradient elution to correct for the fact that solvent compositions can only be changed at fixed instants whereas a linearly changing composition may be desired. Again this can be achieved in the CALC.TAR.% and CALC.REQ.% steps.

Thus if during a suction period it is required to proportion a solvent into the pump and the pump is operating at such a speed that it is not possible to open the proportioning valve for a short enough period to give x%, then it is decided to put x times y% into one piston suction period and then again y piston cycles later and so on to give an average percentage of (x times y)/y = x%.

A running average is used to monitor what has been put into the system and then to work out what is needed to add to the average, during this piston cycle, in order to achieve the required solvent composition. If any of the required proportions are found to be less than the minimum that the proportioning valve can be operated for then it is excluded from the piston cycle for which the calculation is made. The requirement for this proportion will increase automatically each piston cycle until it is large enough to be included.

By using this running average method, proportioning over more than one piston cycle is automatically catered for, for any system flow rates, valve switching times are required percentages.

The suction time and suction volume are related by the rate at which micro stepping pulses are applied to the motor and the calculations can be performed in terms of volume, time or microsteps since the speed of the pistons will be related to the rate of application of micro stepping pulses to the motor by a fixed relationship dependent on the construction of the motor, the cam profiles and the piston dimensions.

It is convenient to use a stepping motor and perform the calculations in terms of microsteps but clearly, with appropriate modifications to the calculations, other types of motor could be used, for example d.c. motors.

We claim:

1. A liquid chromatograph comprising
    a separating column,
    reciprocating pump means including multiple pistons for delivering a liquid to said separating column at a desired flow rate, wherein each of said multiple pistons delivers said liquid during a delivery stroke at the same rate as each other of said multiple pistons during corresponding delivery strokes, and wherein said multiple pistons are arranged to have overlapping delivery strokes,
    motor means for driving said multiple pistons,
    control means including a microprocessor for controlling speed of said motor means, said control means producing control signals to cause at least one of said multiple pistons to advance at a first constant velocity during a first period, wherein at least m of said multiple pistons deliver said liquid to said separating column during said first period,
    said control signals causing said at least one of said multiple pistons to advance at a second constant velocity during a second period, wherein at least m+1 of said multiple pistons deliver said liquid to said separating column during said second period,
    wherein said second constant velocity is m/m+1) times said first constant velocity, where m is an integer and m+1 is at most equal to the total number of said multiple pistons,
    said control means further comprising first means for monitoring delivery pressure of said multiple pistons during each pump cycle, and second means for one of either advancing the instant of change of velocity of said multiple pistons in one pump cycle upon detecting a pressure increase in the previous pump cycle or retarding said instant of change of velocity of said multiple pistons in said one pump cycle upon detecting a pressure decrease in the previous pump cycle.

2. A liquid chromatograph according to claim 1, wherein said microprocessor reacts to interrupt signals being generated to coincide with given points in said pump cycles.

3. A liquid chromatograph according to claim 2, wherein said interrupt signals are generated at beginnings of delivery strokes of each for said multiple pistons, at ends of said delivery strokes for each of said multiple pistons, and at instants of change of for velocity of each of said multiple pistons.

4. A liquid chromatograph according to claim 2 or claim 3, wherein shaft encoding means are disposed for deriving one of said interrupt signals, said shaft encoding means being driven in synchronism with said reciprocating pump means.

5. A liquid chromatograph according to claim 4, wherein said shaft encoding means includes a disc having a single cut-out and an optical detector.

6. A liquid chromatograph according to claim 2 or claim 3, wherein said motor means is an electrical stepping motor, wherein said control means further includes driving circuit means for driving said stepping motor, said driving circuit means receiving stepping pulses from said control means, and wherein at least some of said interrupt signals are generated from a count of the number of said stepping pulses generated by a previous interrupt signal.

7. A liquid chromatograph according to claim 6, wherein said control means further includes a programmable counter, and wherein said microprocessor programs said programmable counter upon each occurrence of said interrupt signal to produce an output causing a next interrupt signal to be generated at a given number of stepping pulses later.

8. A liquid chromatograph according to claim 7, wherein the interrupt signal generated at beginnings of delivery strokes of each of said multiple pistons initiates calculation of said instant of change of velocity after beginning of a delivery stroke for the next piston of said multiple pistons.

9. A liquid chromatograph according to claim 8, wherein said instant of change of velocity is advanced or retarded by a time proportional to the magnitude of said pressure increase or said pressure decrease.

10. A liquid chromatograph according to claim 9, wherein said instant of change of velocity is advanced or retarded by kMp steps of said stepping motor, where k is a constant and Mp is the magnitude of pressure increase or pressure decrease at an output of said reciprocating pump means.

11. A liquid chromatograph according to claim 1 or claim 2 or claim 3, wherein said instant of change of velocity is advanced or retarded by a time proportional to the magnitude of said pressure increase or said pressure decrease.

12. A liquid chromatograph according to claim 1 or claim 2 or claim 3, wherein upon increasing said desired flow rate said instant of change of velocity of said multiple pistons is retarded during a next cycle by a factor dependent on the change in flow rate, and wherein upon decreasing said desired flow rate said instant of change of velocity of said multiple pistons is advanced during a next cycle by a factor dependent on the change in flow rate.

13. A liquid chromatograph according to claim 1 or claim 2 or claim 3, wherein said second period is terminated earlier upon increasing said desired flow rate, and said second period is terminated later upon increasing delivery pressure.

14. A liquid chromatograph according to claim 1, claim 2 or claim 3, wherein said reciprocating pump means is a dual piston pump.

15. A liquid chromatograph according to claim 1 or claim 2 or claim 3, wherein said motor means drives said multiple pistons with a cam structure.

16. A liquid chromatograph according to claim 15, wherein said cam structure includes a separate cam for each piston and a common shaft for mounting each of said separate cams or forming integrally each of said separate cams.

17. A liquid chromatograph according to claim 16, wherein each of said separate cams is profiled to produce a constant linear velocity for each piston by a constant angular velocity of said separate cam.

* * * * *